US008512774B2

(12) United States Patent
Eyal

(10) Patent No.: US 8,512,774 B2
(45) Date of Patent: Aug. 20, 2013

(54) FERMENTATION PROCESSES

(75) Inventor: Aharon Eyal, Jerusalem (IL)

(73) Assignee: Eyal Research Consultants Ltd, Jerusalem (IL)

( * ) Notice: Subject to any disclaimer, the term of this patent is extended or adjusted under 35 U.S.C. 154(b) by 0 days.

(21) Appl. No.: 13/203,921

(22) PCT Filed: Mar. 2, 2010

(86) PCT No.: PCT/IL2010/000169
§ 371 (c)(1),
(2), (4) Date: Aug. 30, 2011

(87) PCT Pub. No.: WO2010/100642
PCT Pub. Date: Sep. 10, 2010

(65) Prior Publication Data
US 2011/0312045 A1    Dec. 22, 2011

Related U.S. Application Data

(60) Provisional application No. 61/156,935, filed on Mar. 3, 2009.

(30) Foreign Application Priority Data

Feb. 28, 2010 (IL) .......................................... 204214

(51) Int. Cl.
*C12C 7/00*    (2006.01)
*C12P 7/10*    (2006.01)

(52) U.S. Cl.
USPC ............................................. 426/30; 435/165

(58) Field of Classification Search
USPC ............................................. 435/165; 426/30
See application file for complete search history.

(56) References Cited

U.S. PATENT DOCUMENTS

2009/0084025 A1 *    4/2009    Bhatia et al. .................... 44/307

FOREIGN PATENT DOCUMENTS

WO    WO2008144878    * 12/2008

* cited by examiner

*Primary Examiner* — Maryam Monshipouri
(74) *Attorney, Agent, or Firm* — Lucas & Mercanti, LLP

(57) ABSTRACT

The present invention provides a method for the production of at least one of a fermentation product and a derivate thereof comprising the steps of: a. providing a fermentable aqueous solution comprising at least one fermentable compound and at least one impurity; b. selectively extracting the at least one impurity from at least a portion of the fermentable aqueous solution by means of an extractant to form an impurity-depleted fermentable solution comprising a fermentable compound and to form an impurity-comprising extract; and c. fermenting the fermentable compound of the impurity-depleted fermentable solution to form a fermentation broth comprising a fermentation product wherein the extractant comprises at least one of the fermentation product and a derivate thereof.

19 Claims, No Drawings

FERMENTATION PROCESSES

This application is a 371 of PCT/IL2010/000169 filed on Mar. 2, 2010, which claims the benefit of U.S. Provisional Application No. 61/156,935 filed on Mar. 3, 2009 and Israeli Patent Application No. 204214 filed on Feb. 28, 2010, the contents of each of which are incorporated herein by reference.

BACKGROUND OF THE INVENTION

Fermentation processes are used for the production of food ingredients, feed ingredients, biofuels, such as ethanol, and other industrial chemicals. Fermentation processes require a supply of fermentable compounds. Presently, fermentable compounds are derived almost solely from starch crops and sugarcane. Such sources are of limited supply and of relatively high cost, limiting the ability to produce fermentation products at economically attractive prices, on the one hand, and increasing the prices of food, on the other.

Major effort has been expended in the development of fermentable compounds from alternative sources that are much more abundant and involve lower costs. Examples of such fermentable compounds are cellulosic compounds or lignocellulosic compounds, such as wood, agricultural residues, sugarcane bagasse, energy crops, residues from wood processing, etc., all of which are characterized in comprising polysaccharides, such as hemicellulose and cellulose. For effective fermentation, such polysaccharides ideally are hydrolyzed. Hydrolysis, particularly cellulose hydrolysis, requires relatively harsh conditions, such as the use of a high acid concentration and elevated temperatures. Under such harsh conditions, undesirable degradation occurs, in particular, of hydrolysis products such as hexoses and pentoses, but also of lignin, when present. Such degradation of hydrolysis products generates impurity degradation products, some of which are inhibitory to fermentation and thereby reducing the fermentation product yield. Such fermentation inhibitors include furfural, hydroxymethylfurfural and acetic acid.

While many methods have been proposed for the removal of such inhibitors from the fermentable compounds in order to minimize such inhibition, none are ideal. Treatments such as distillation, adsorption, addition of a base, overliming, contacting with an ion-exchanger and extracting with a solvent, for example, are all costly and present other difficulties as will be appreciated by the skilled artisan.

This invention provides, inter alia, relatively pure fermentable compounds, which are prepared by a process which removes fermentation inhibitors from solutions of fermentable compounds, and which method is cost-effective.

SUMMARY OF THE INVENTION

The present invention provides a method for the production of at least one of a fermentation product and a derivate thereof comprising the steps of: (a) providing a fermentable aqueous solution comprising at least one fermentable compound and at least one impurity; (b) selectively extracting said at least one impurity from at least a portion of said fermentable aqueous solution by means of an extractant to form an impurity-depleted fermentable solution comprising a fermentable compound and to form an impurity-comprising extract; and (c) fermenting said fermentable compound of said impurity-depleted fermentable solution to form a fermentation broth comprising a fermentation product, wherein said extractant comprises at least one of said fermentation product and a derivate thereof.

The method of the present invention involves providing a fermentable aqueous solution comprising at least one fermentable compound and at least one impurity. As used herein, the term "fermentable compound" (or "fermentable") means any carbon compound which may be metabolized by a microorganism. The term "fermentable aqueous solution" refers to an aqueous solution comprising a fermentable compound.

The terms "provided fermentable aqueous solution" and "provided solution" are to be understood to be synonymous. The terms "fermentation process" and "fermenting" are also to be understood to be synonymous.

Typically, in conducting a fermentation process, microorganisms are cultured in a medium, typically aqueous, comprising at least one fermentable compound and optionally other nutrients, which medium is referred to as "fermentation medium". The fermentation medium could be a clear aqueous solution or may contain a suspension of another phase, e.g. solid or liquid.

As used herein the term "impurity" means a compound other than a fermentable compound. According to an embodiment, the impurity in said provided fermentable aqueous solution is a fermentation inhibitor.

According to this aspect of the invention and in one embodiment thereof, the method further comprises the step of converting said fermentation product to form a derivate.

According to another embodiment of the invention, the impurity is at least one of pentose degradation products, hexose degradation products and lignin degradation products. According to another embodiment, the impurity is selected from a group consisting of furfural, hydroxymethylfurfural, furans, acetic acid, phenolic compounds and combinations thereof.

According to an embodiment of the invention, the at least one of said fermentation product and a derivate thereof is water-insoluble and is selected from the group consisting of fatty acid esters, fatty alcohols, olefins, hydrocarbons, products of oligomerization and combinations thereof.

According to an embodiment of the invention, the providing comprises an acid treatment of cellulosic material. According to other embodiments of the invention, the providing comprises thermal treatment of cellulosic material and said thermal treatment of cellulosic material is conducted in the presence of water and of an acid.

According to another embodiment of the invention, at least a portion of said provided solution is acidic in said extracting in step (b). According to another embodiment the provided fermentable aqueous solution comprises a soluble fermentable compound at a concentration of at least 10% wt.

According to an embodiment of the invention, the method further comprises separating said impurity from said impurity-comprising extract to form a separated impurity and a regenerated extractant. According to other embodiments, the impurity-comprising extract is used as such or after some treatment and according to a specific embodiment, the impurity-comprising extract is used to provide energy.

According to an embodiment of the invention, the method further comprises the step of removing said impurity from at least one of said provided fermentable solution and said impurity-depleted fermentable solution. According to a related embodiment, the step of impurity removal comprises distillation, adsorption, active carbon treatment, heat treatment, addition of a base, overliming, contacting with an ion-exchanger, extracting with an extractant other than said fermentation product and a derivate thereof, membrane separation and combinations thereof.

As used herein, the term "fermentation inhibitor" (or "inhibitor") means a compound or a combination of compounds that, when present in fermentation medium, inhibits fermentation. Thus, according to various embodiments, in comparing a first fermentation medium containing no fermentation inhibitor to a second fermentation medium of identical composition to which an inhibitor was added to a concentration greater than a threshold level, the fermentation occurring in the latter is at a slower rate, reaches a lower product titer (i.e. lower final product concentration), is characterized by a slower microorganism growth or any combination of the same. The effect of a fermentation inhibitor might not be observed when present at a low concentration, but effects were reported for inhibitors of concentrations as low as 0.1% wt ("threshold concentration").

Any fermentable aqueous solution comprising at least one fermentable compound and at least one impurity, such as a fermentation inhibitor, is suitable for use in the methods of the present invention. According to one embodiment, the fermentable aqueous solution is a product of treating a cellulosic material. As used herein the term "cellulosic material" means material comprising cellulose, which cellulose could be in crystalline form, amorphous form or a combination of both, e.g. waste paper, manure, etc. The cellulosic material may also comprise lignin. Material comprising both cellulose and lignin is referred to herein as cellulosic material, "lignocellulosic material" or "biomass". Typically lignocellulosic material comprises also hemicellulose and other components, such as ash. Any lignocellulosic material is suitable for the present invention, e.g. wood, wood chips, agricultural residues, such as straw, corn stalk and corn cobs, sugarcane bagasse, leaves, switchgrass energy crops, etc.

Cellulose and hemicellulose are polysaccharides. According to an embodiment of the present invention, providing the fermentable aqueous solution comprises hydrolyzing at least one of cellulose and hemicellulose to form oligosaccharides and/or monosaccharides. The products of hydrolyzing cellulose comprise glucose and/or glucose-containing oligomers. Glucose is one of the six-carbon sugars also referred to as hexoses. According to an embodiment, said fermentable aqueous solution further comprises other hexoses, such as galactose, fructose and mannose. The products of hydrolyzing hemicellulose comprise at least one of xylose, arabinose and/or oligomers containing those sugars. Xylose and arabinose are two of the five-carbon sugars also referred to as pentoses.

It is to be understood that any hydrolysis method is envisioned, including biologically catalyzed methods, e.g. by the use of suitable enzymes, chemically catalyzed methods, e.g. by an acid or any combination thereof. Thus, according to an embodiment, the cellulosic material may be pre-treated, after which enzymatic hydrolysis is conducted. Typically, such pre-treatment involves at least partial hydrolysis, e.g. of hemicellulose, where present. Optionally, pre-treatment involves some lignin removal (also referred to as "delignification"), extraction of hemicellulose and/or at least partial decrystallization of crystalline cellulose. According to an embodiment, providing comprises an acid hydrolysis or acid pre-treatment of cellulosic material, typically with a strong acid, such as sulfuric, hydrochloric, nitric or phosphoric acid.

According to an embodiment of the method of the present invention, chemical catalysis, e.g. acid hydrolysis and/or pre-treatment involves thermal treatment. As used herein the term "thermal treatment" means any treatment of cellulosic material conducted at elevated temperature, including chemically catalyzed hydrolysis and pre-treatment. According to an embodiment of the invention, the thermal treatment of cellulosic material is conducted in the presence of water, the presence of an acid or both. In one embodiment, thermal treatment is conducted in the presence of an acid, typically a strong acid, whether mineral such as sulfuric, hydrochloric, nitric or phosphoric acid or an organic acid, e.g. sulfonic acid. According to various publications, the elevated temperature facilitates the acid-catalyzed hydrolysis reaction. In another embodiment, no auxiliary acid is added, but thermal treatment in the presence of moisture forms an acid, e.g. due to some degradation of lignin in lignocellulosic material. Such acid is then active in hydrolysis. In some embodiments, said acid is mainly acetic acid. In some embodiments, the cellulosic material comprises crystalline cellulose, and conducting hydrolysis of the same at elevated temperatures facilitates hydrolysis through the decrystallization of crystalline cellulose. According to various embodiments, the thermal treatment is conducted at a temperature of at least 100° C., at least 160° C., or at least 190° C., e.g., a preferred range of from about 100-250° C. According to another embodiment, the thermal treatment is conducted under pressure e.g., a pressure suitable to prevent boiling of water at the chosen temperature.

In the methods of the present invention, the provided aqueous solution is contacted with an extractant, whereupon an impurity, such as a fermentation inhibitor, is extracted therefrom. As used herein, the terms "contacted" or "contacting" also means "extracted" or "extracting", respectively. As used here, the term "extractant" means an organic liquid (also referred to as solvent) with limited solubility in water that selectively extracts the impurity, e.g. fermentation inhibitor, over the fermentable compound. According to an embodiment, the extractant is water insoluble. According to the present invention, the extractant comprises at least one of said fermentation product and a derivate thereof. According to an embodiment, the solubility of said at least one of said fermentation product and a derivate thereof in water at 25° C. is less than 10%, preferably less than 5%, more preferably less than 2% and most preferably less than 1%. According to another embodiment, the solubility of water in said at least one of said fermentation product and a derivate thereof at 25° C. is less than 10%, preferably less than 5%, more preferably less than 2% and most preferably less than 1%.

In preferred embodiments, said at least one of said fermentation product and a derivate thereof dissolves in said impurity-depleted fermentable solution comprising said fermentable compound, and said solubility is less than 2%, preferably less than 1% and more preferably less than 0.5%.

In preferred embodiments of the present invention, said method further comprises separating said impurity from said impurity-comprising extract to form separated impurity and a regenerated extractant. According to various embodiments, said separating comprises at least one of the steps of distillation, adsorption, active carbon treatment, heat treatment, addition of a base contacting with an ion-exchanger, addition or removing a solvent, membrane separation and combinations thereof In preferred embodiments, said impurity-comprising extract is used as such or after a treatment thereof.

In other preferred embodiments, said impurity-comprising extract is used to provide energy, as such or after a treatment thereof. According to an embodiment, said impurity-comprising extract is used as a biofuel, biodiesel, as an ingredient of biofuel, e.g. in blends with another fuel, as an ingredient of biodiesel, e.g. in blends with diesel, a precursor of a biofuel, a precursor of a biodiesel and combinations thereof.

In especially preferred embodiments, said provided fermentable aqueous solution comprises a soluble fermentable compound at a concentration of at least 10% wt, preferably at least 15% wt and more preferably at least 20% wt.

It is to be understood that the methods of this invention encompass any form of contacting the provided aqueous solution with the extractant, such as, but not limited to, contact in a single step or in multiple steps. In some embodiments, contacting in multiple steps may be through the use of a counter-current mode.

In some embodiments, the contacting is conducted in a contacting vessel in which the two liquids are mixed to form droplets of one of the phases dispersed in the other phase. Mass transfer of the extracted impurity, e.g. an inhibiting compound from the aqueous solution to the extractant is typically conducted through the surface of those droplets. Typically, the phases are then allowed to settle. According to some embodiments, in the contacting vessel, mixing and settling are conducted in two separate zones. Settling forms an organic solution comprising the extractant and the extracted impurity, which is referred to as the "impurity-comprising extract", or just the "extract". Also formed is an aqueous solution comprising the fermentable compound and less impurity or no impurity at all, which solution is referred to as "impurity-depleted fermentable solution comprising a fermentable compound" or just the "impurity-depleted fermentable solution" or "impurity-depleted solution". According to an embodiment of the method, the impurity-comprising extract is then separated from the impurity-depleted solution.

As indicated, extraction is selective. According to various embodiments, the w/w ratio between the impurity, e.g. a fermentation inhibitor, and the fermentable compound in the impurity-comprising extract is greater than that ratio in the impurity-depleted solution by at least 5-fold, 50-fold or 100-fold, or greater. According to other embodiments, the w/w ratio between the impurity, e.g. a fermentation inhibitor, and the fermentable compound in the impurity-comprising extract is greater than that ratio in the provided fermentable aqueous solution by at least 5-fold, 50-fold or 100-fold, or greater.

According to one embodiment, providing comprises a treatment, which treatment comprises acid treatment, thermal treatment or a combination thereof.

In a first embodiment, said providing comprises an acid treatment of cellulosic material.

In another embodiment, said providing comprises thermal treatment of cellulosic material.

Preferably, in said other embodiment, said thermal treatment of cellulosic material is conducted in the presence of water and of an acid.

In preferred embodiments, in said extracting, said at least a portion of said provided solution is acidic.

According to an embodiment, said treatment is at least partially conducted in a treatment vessel, and extracting the impurity is conducted simultaneously with the treatment. According to one option of that embodiment, contacting is conducted in the same vessel as the treatment. According to another, a portion of an aqueous solution formed in the treatment is withdrawn from the treatment vessel into another vessel where contacting takes place. After said extracting, optionally a fraction of the formed impurity-depleted solution is transferred back to the treatment vessel. According to another embodiment, contacting is conducted after the treatment is finished and the impurity-depleted solution is used to form the fermentation medium. According to an embodiment, treatment uses a catalyst, such as an acid and contacting is conducted in the presence of said catalysts. According to another embodiment, said catalyst is removed prior to said contacting. According to still another embodiment, the provided aqueous solution is used to form the fermentation medium and extracting of the impurity is conducted by contacting the extractant with said fermentation medium. Alternatively, or in addition, extracting of the impurity is conducted by contacting the extractant with the fermentation broth. According to still another embodiment, a combination of these embodiments is used. According to an embodiment, extracting is conducted in equipment typically used in industrial solvent extraction processes, e.g. mixer-settlers, centrifugal contactors and pulsating columns, as know to people versed in the art of solvent extraction.

According to an embodiment, the method of the present invention further comprises a step of impurity, preferably fermentation inhibitor, removal from at least one of said provided fermentable solution, said impurity-depleted fermentable solution and said fermentation medium. Preferably, said step of impurity removal comprises distillation, adsorption, active carbon treatment, heat treatment addition of a base, overliming, contacting with an ion-exchanger, extracting with an extractant other than said fermentation product or derivate thereof, another extracting with said fermentation product or derivate thereof, membrane separation and combinations thereof.

The method of the present invention further comprises the step of fermenting said fermentable compound of said impurity-depleted fermentable solution to form an aqueous solution comprising a fermentation product, which solution is also referred to as "fermentation broth". The fermentable compound is typically fermented in a fermentation medium. According to an embodiment of the invention such fermentation medium is formed from the impurity-depleted solution via required adjustments. Such adjustments may include dilution or concentration, another step of inhibitor removal, if required, addition of nutrients, such as a nitrogen source, minerals, vitamins and growth factors, pH adjustment, catalyst removal, temperature adjustment, removal of residual extractant, and others, as will be appreciated by the skilled artisan.

According to an embodiment, said at least one of said fermentation product and a derivate thereof dissolves in said impurity-depleted fermentable solution during said extracting of said impurity. According to an embodiment, said solubility at 25° C. is less than 2%, preferably less than 1% and more preferably less than 0.5%. According to an embodiment, said fermentation medium is formed from said impurity-depleted solution and comprises at least one of said fermentation product and a derivate thereof and fermentation of the comprised fermentable compound is efficient. According to an embodiment, fermentation in a fermentation medium formed from the extracted impurity-depleted solution formed according to the method of the present invention has better performance, e.g. higher yield and/or higher titer, compared with fermentation in a fermentation medium formed from the provided solution with no such extraction. According to an embodiment, said better performance is characterized by a yield that is at least 2% greater, preferably at least 5% and more preferably at least 10% greater. According to an embodiment, said better performance is characterized by a titer that is at least 2% greater, preferably at least 5% and more preferably at least 10% greater compared with fermentation in a fermentation medium formed from the provided solution with no such extraction The cultured microorganisms in the fermentation medium metabolize the fermentable compound in the fermentation medium and form at least one product referred to as fermentation product. A fermentation medium comprising a fermentation product is also referred to as fermentation broth. In some embodiments, the fermentation product is secreted (i.e. an extracellular fermentation product), or in some embodiments, the fermentation product is intracellularly located, or in some embodiments, the fermentation product is cell wall or membrane-associated, or in some embodiments, the fermentation product may be any combination thereof. According to different embodiments, the fermentation product is water soluble or water insoluble. As used here, the term water insoluble means that its solubility in water at 25° C. is less than 2%, preferably less than 1% wt. A water insoluble fermentation product, if excreted from the cell, may form a separate liquid or solid phase in the fermentation broth.

According to an embodiment of the method, the fermentation product is separated from the fermentation broth to form separated fermentation product, also referred to as separated product. Separation uses, according to various embodiments, distillation, extraction, crystallization, membrane separation, ion-exchange, adsorption, chromatography and various combinations of those. According to an embodiment of the method, the fermentation product is extra-cellular and water insoluble and as such forms a separate phase in the fermentation broth, e.g. a liquid organic phase or a solid precipitate. In case of such separate phase formation, said separation involves according to various embodiments, decantation, centrifugation, filtration, use of cyclone separators, membrane separation and combinations of those. According to another embodiment of the invention, the fermentation product is intra-cellular and product separation comprises liberation of the product from the cell, e.g. via extraction, increasing the rate of diffusion through the cell membrane, opening up of the cell and various combinations of those. According to a related embodiment, the fermentation product is intracellular and water insoluble, product liberation from the cell is conducted in an aqueous medium and the liberated fermentation product forms a separate phase in said aqueous medium. According to said embodiment, separation of said liberated product comprises decantation, centrifugation, filtration, use of cyclone separators, membrane separation and combinations of those.

Typically, separation includes at least one of product concentration and product purification, or a combination thereof. Typically, the product concentration in the broth is quite small, limited by product inhibition to less than 20% wt, less than 10% wt or less than 5% wt. In cases of an intracellular product or an insoluble extra-cellular product, the product concentration means the fraction of the product in the fermentation broth at the end of the fermentation. Product concentration involves product separation from water to reach product concentrations greater than 50% wt, greater than 70% wt or greater than 90% wt. Product purification (also referred to as "purification") removes at least one impurity. As used here, the term impurity refers to any compound other than the fermentation product and water. In some fermentation processes multiple fermentation products are formed and in some embodiments, impurities of such processes may include fermentation products other than those of commercial interest. In some embodiments, the separated product concentration is greater than 80% wt, greater than 92% wt or greater than 98% wt, on a water-free basis.

The separated product could be used as such or further processed. Any processed product is referred to herein as "product derivate" or "derivate". Product processing comprises, according to various embodiments, purification, concentration, mixing with a solvent to form a solution in that solvent, adding at least one compound to the separated product or its solution, pH adjustment, and combinations of those. Product processing—and derivate formation—comprises, according to other embodiments, chemical conversion. Any chemical conversion is suitable for the purpose of the present invention. According to various embodiments, such chemical conversion comprises hydrolysis, esterification, hydration, dehydration, hydrogenation, oxidation, reduction, oligomerization and various combinations thereof. According to an embodiment of the method, said product derivate is further processed to form its derivates, which are also referred to as product derivates or derivates.

Thus, according to one embodiment, the fermentation product is an alcohol and said alcohol is reacted with an acid, e.g. an organic acid, to form the corresponding ester. According to another embodiment, the fermentation product is an organic acid and said acid is reacted with an alcohol to form the corresponding ester. The organic acid of those esters is, according to various embodiments, a water-soluble carboxylic acid, e.g. acids having up to six carbon atoms, or a fatty, insoluble one, e.g. acid having more than six carbon atoms, such as palmitic acid, stearic, oleic acid or linoleic acid. The alcohol of those esters is, according to various embodiments a mono- or poly-hydroxyl alcohol, a short-chain water soluble one or a fatty alcohol. According to various embodiments, said alcohol is selected from the group consisting of methanol, ethanol, propanol, butanol, ethylene glycol, glycerol and various isomers thereof. According to those embodiments, the derivate is selected from a group comprising esters of carboxylic and fatty acids, e.g. ethyl acetate, ethyl butyrate, ethyl succinate, butyl acetate, ethyl or methyl palmitate, butyl palmitate, ethyl or methyl oleate, ethyl or methyl stearate and combinations thereof. According to another embodiment, the fermentation product is an organic acid and said acid is reacted with an amine to form the corresponding amide. According to another embodiment, the fermentation product is an olefin or the derivate is an olefin (e.g. as formed by dehydration of alcohol fermentation product) and said olefin is oligomerized to form an olefin of higher molecular weight.

Alternatively, converting the fermentation product to the derivate is conducted before product separation from the fermentation broth, i.e. while the fermentation product is still in the fermentation broth as such or after some modification. According to that embodiment, the product derivate is formed in the fermentation broth, or in the modified fermentation broth, and optionally separated from said broth or modified broth by means of known separation processes. According to various embodiments, the formed product derivate is water soluble, has partial water solubility or is water insoluble. According to various embodiments, separation of the product derivate comprises distillation, extraction, crystallization, membrane separation, ion-exchange, adsorption, chromatography, decantation, centrifugation, filtration, use of cyclone separators, and combinations of those. Separation of said product derivate forms a separated product derivate.

According to the method of the present invention, the impurity, e.g. a fermentation inhibitor is extracted from at least a portion of the provided aqueous solution by means of an extractant and said extractant comprises at least one compound selected from the group consisting of the fermentation product, the separated fermentation product, the product derivate and the separated product derivate. According to an embodiment, said at least one compound is further treated before using as extractant, e.g. purified, further chemically converted and mixed with another compound. According to an embodiment, the compound is selected from a group consisting fatty acids, fatty acid esters, fatty alcohols, fatty alcohol esters, olefins, hydrocarbons, products of oligomerization and combinations thereof.

According to the present invention, it has now been found that, under certain conditions, impurity extraction is enhanced at an acidic pH and/or in the presence of a high concentration of fermentable compound. Thus, according to an embodiment of the method of the present invention, upon extracting said impurity, said at least a portion of said provided solution is acidic, or rendered acidic, e.g. having a pH lower than 6, preferably lower than 5.5 more preferably lower than 5. According to another embodiment, upon extracting said impurity, said at least a portion of said provided solution has a pH of between 3 and 6.6, preferably 3.5 and 6 and more preferably between 4 and 5.5 .According to one embodiment, providing a fermentable aqueous solution comprises acid-catalyzed hydrolysis or cellulose, hemicellulose or both, forming a hydrolyzate aqueous solution comprising fermentable compound and the catalyzing acid. According to various embodiments, the impurity is extracted from that hydrolyzate aqueous solution as such or after partial removal of the acid to reach the desired pH. According to another embodiment, the provided aqueous solution is neutral or basic and acid is added to it prior to extraction in order to reach the preferred pH. According to an embodiment of the method, at the time of impurity extraction, the concentration of soluble fermentable compound in said provided solution is at least 10% wt, preferably at least 15% wt, most preferably at least 20% wt.

According to a method of the present invention, an impurity-comprising extract is formed. According to one embodiment, at least a fraction of the impurity is separated from said extract to form separated impurity and an organic phase, which organic phase is used for further extraction of impurity (also referred to as regenerated extractant) or for another application. The separated impurity is used, according to various embodiments, for energy, as such, as a precursor for the formation of other chemicals or a combination thereof. Alternatively, or in addition, at least a fraction of the impurity-comprising extract is used as such or after some modification. According to an embodiment, the fermentation product or its derivate is used for providing energy, e.g. as a biofuel and the impurity comprised in the extract adds to its energy content and/or improves its performance. According to still another embodiment, the impurity is chemically modified while still in the extract to form an extract comprising modified impurity and that extract is used as such or further treated for separation of the modified impurity.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLES

Example 1

A 30% carbohydrates aqueous solution was prepared. That solution also contained 3.3% furfural. That aqueous solution was contacted with octanol at organic/aqueous w/w ratio of 1 .The phases were equilibrated by intensive mixing at 25° C. and allowed to settle. The phases were then separated and analyzed. The furfural concentrations in the organic and aqueous phases were 2.7% and 0.61%, respectively. These results show an efficient extraction i.e., a distribution co-efficient of 4.5, which means extraction of about 80% of the furfural in a single stage at relatively low extractant/feed ratios.

Example 2

An aqueous solution as in Example 1 was equilibrated with ethyl caproate (the ethyl ester of caproic acid) using the same method and same conditions as in Example 1 .The furfural concentrations in the organic and aqueous phases were 3.0% and 0.3%, respectively. These results show even more efficient extraction than in the case of octanol, i.e., a distribution co-efficient of 10, which means extraction of about 90% of the furfural in a single stage at relatively low extractant/feed ratios.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A method comprising the steps of:
   a. providing a fermentable aqueous solution comprising at least one fermentable compound and at least one impurity;
   b. selectively extracting said at least one impurity from at least a portion of said fermentable aqueous solution by means of an extractant to form an impurity-depleted fermentable solution comprising a fermentable compound and to form an impurity-comprising extract;
   c. fermenting said fermentable compound of said impurity-depleted fermentable solution to form a fermentation broth comprising a fermentation product soluble in said broth; and
   d. converting said fermentation product to form a derivate with a solubility of less than 2% in said impurity-depleted fermentable solution.

2. The method of claim 1, wherein said impurity is a fermentation inhibitor.

3. The method of claim 1, wherein said impurity is at least one of pentose degradation products, hexose degradation products and lignin degradation products.

4. The method of claim 1, wherein said impurity is selected from a group consisting of furfural, hydroxymethylfurfural, furans, acetic acid, phenolic compounds and combinations thereof.

5. The method of claim 1, wherein said derivate is water-insoluble and is selected from the group consisting of fatty acid esters, fatty alcohols, olefins, hydrocarbons, products of oligomerization and combinations thereof.

6. The method of claim 1, wherein the w/w ratio between the impurity and the fermentable compound in the impurity-comprising extract is greater than that ratio in the impurity-depleted solution by at least 5-fold.

7. The method of claim 1, wherein said providing comprises an acid treatment of cellulosic material.

8. The method of claim 1, wherein said providing comprises thermal treatment of cellulosic material.

9. The method of claim 8, wherein said thermal treatment of cellulosic material is conducted in the presence of water and of an acid.

10. The method of claim 1, wherein in said extracting in step (b), said at least a portion of said provided solution is acidic.

11. The method of claim 1, further comprising separating said impurity from said impurity-comprising extract to form separated impurity and a regenerated extractant.

12. The method of claim 1, wherein said impurity-comprising extract is used as such or after a treatment thereof.

13. The method of claim 1, wherein said impurity-comprising extract is used to provide energy, as such or after a treatment thereof 14. The method of claim 1, further comprising a step of impurity removal from at least one of said provided fermentable solution and said impurity-depleted fermentable solution.

15. The method of claim 14, wherein said step of impurity removal comprises at least one of the steps of distillation, adsorption, active carbon treatment, heat treatment, addition of a base, overliming, contacting with an ion-exchanger, extracting with an extractant other than said fermentation product and a derivate thereof, membrane separation and combinations thereof.

16. The method of claim 1, wherein said provided fermentable aqueous solution comprises a soluble fermentable compound at a concentration of at least 10% wt.

17. The method of claim 1, wherein said extractant comprises a derivate of said fermentation product.

18. The method of claim 1, wherein said extractant comprises a portion of said derivate of said fermentation product.

19. The method of claim 1, further comprising step (e): combining a portion of said derivate of said fermentation product with said extractant for use in said selective extraction step (b).

* * * * *